(12) United States Patent
Martin et al.

(10) Patent No.: US 6,235,279 B1
(45) Date of Patent: *May 22, 2001

(54) METHOD FOR TREATING THROMBOEMBOLIC CONDITIONS BY INHIBITING REOCCLUSION VIA THE USE OF MULTIPLE BOLUS ADMINISTRATION OF THROMBOLYTICALLY ACTIVE PROTEINS

(75) Inventors: Ulrich Martin, Mannheim (DE); Reinhard König, San Carlos, CA (US)

(73) Assignee: Boehringer Mannheim GmbH, Mannheim (DE)

( * ) Notice: Subject to any disclaimer, the term of this patent is extended or adjusted under 35 U.S.C. 154(b) by 0 days.

This patent is subject to a terminal disclaimer.

(21) Appl. No.: 08/794,528

(22) Filed: Feb. 3, 1997

Related U.S. Application Data

(62) Continuation of application No. 08/217,616, filed on Mar. 25, 1994, now Pat. No. 5,690,931, which is a continuation-in-part of application No. 08/137,116, filed as application No. PCT/EP92/00851 on Apr. 15, 1992, now Pat. No. 5,500,411.

(30) Foreign Application Priority Data

Jul. 18, 1991 (DE) .................................................. 41 23 845
Apr. 15, 1992 (DE) .................................................. 41 12 398

(51) Int. Cl.$^7$ ............................ A61K 38/48; A61K 38/49
(52) U.S. Cl. .................................... 424/94.63; 424/94.64; 435/212; 435/219; 435/226
(58) Field of Search .............................. 424/94.63, 94.64; 435/172.3, 212, 215, 216, 219, 226; 514/12

(56) References Cited

U.S. PATENT DOCUMENTS 5,500,411 * 3/1996 Martin et al. ........................... 514/12

OTHER PUBLICATIONS

Cercek et al. "Enhancement of thrombolysis with tissue–type plasminogen activator by pretreatment with heparin" Circulation 74(3), 583–587, Sep. 1986.*

* cited by examiner

Primary Examiner—Robert A. Wax
Assistant Examiner—Nashaat T. Nashed
(74) Attorney, Agent, or Firm—Fulbright & Jaworski

(57) ABSTRACT

Discussed are therapeutic approaches to the treatment of thrombolic conditions. The therapies use thrombolytically active proteins which inhibit reocclusion in the subject. The proteins are administered in two or more boli.

12 Claims, 8 Drawing Sheets

SEQUENCE LISTING (1) GENERAL INFORMATION:

(iii) NUMBER OF SEQUENCES: 1

(2) INFORMATION FOR SEQ ID NO: 1:

(i) SEQUENCE CHARACTERISTICS:
      (A) LENGTH: 355 amino acids
      (B) TYPE: amino acids
      (D) TOPOLOGY: linear (xi) SEQUENCE DESCRIPTION: SEQ ID NO: 1:

```
Ser Tyr Gln Gly Asn Ser Asp Cys Tyr Phe Gly Asn Gly Ser Ala Tyr
                  5                  10                  15

Arg Gly Thr His Ser Leu Thr Glu Ser Gly Ala Ser Cys Leu Pro Trp
             20                  25                  30

Asn Ser Met Ile Leu Ile Gly Lys Val Tyr Thr Ala Gln Asn Pro Ser
             35                  40                  45

Ala Gln Ala Leu Gly Leu Gly Lys His Asn Tyr Cys Arg Asn Pro Asp
     50                  55                  60

Gly Asp Ala Lys Pro Trp Cys His Val Leu Lys Asn Arg Arg Leu Thr
65                  70                  75                  80

Trp Glu Tyr Cys Asp Val Pro Ser Cys Ser Thr Cys Gly Leu Arg Gln
                 85                  90                  95
```

-continued

```
Tyr Ser Gln Pro Gln Phe Arg Ile Lys Gly Gly Leu Phe Ala Asp Ile
            100             105             110

Ala Ser His Pro Trp Gln Ala Ala Ile Phe Ala Lys His Arg Arg Ser
            115             120             125

Pro Gly Glu Arg Phe Leu Cys Gly Gly Ile Leu Ile Ser Ser Cys Trp
            130             135             140

Ile Leu Ser Ala Ala His Cys Phe Gln Glu Arg Phe Pro Pro His His
145             150             155             160

Leu Thr Val Ile Leu Gly Arg Thr Tyr Arg Val Val Pro Gly Glu Glu
            165             170             175

Glu Gln Lys Phe Glu Val Glu Lys Tyr Ile Val His Lys Glu Phe Asp
            180             185             190

Asp Asp Thr Tyr Asp Asn Asp Ile Ala Leu Leu Gln Leu Lys Ser Asp
            195             200             205

Ser Ser Arg Cys Ala Gln Glu Ser Ser Val Val Arg Thr Val Cys Leu
            210             215             220

Pro Pro Ala Asp Leu Gln Leu Pro Asp Trp Thr Glu Cys Glu Leu Ser
225             230             235             240

Gly Tyr Gly Lys His Glu Ala Leu Ser Pro Phe Tyr Ser Glu Arg Leu
            245             250             255

Lys Glu Ala His Val Arg Leu Tyr Pro Ser Ser Arg Cys Thr Ser Gln
            260             265             270

His Leu Leu Asn Arg Thr Val Thr Asp Asn Met Leu Cys Ala Gly Asp
            275             280             285

Thr Arg Ser Gly Gly Pro Gln Ala Asn Leu His Asp Ala Cys Gln Gly
    290             295             300

Asp Ser Gly Gly Pro Leu Val Cys Leu Asn Asp Gly Arg Met Thr Leu
305             310             315             320

Val Gly Ile Ile Ser Trp Gly Leu Gly Cys Gly Gln Lys Asp Val Pro
            325             330             335

Gly Val Tyr Thr Lys Val Thr Asn Tyr Leu Asp Trp Ile Arg Asp Asn
            340             345             350

Met Arg Pro
        355
```

METHOD FOR TREATING THROMBOEMBOLIC CONDITIONS BY INHIBITING REOCCLUSION VIA THE USE OF MULTIPLE BOLUS ADMINISTRATION OF THROMBOLYTICALLY ACTIVE PROTEINS

RELATED APPLICATIONS

This application is a continuation of Ser. No. 08/217,616 filed Mar. 25, 1994, now U.S. Pat. No. 5,690,931, which in turn is a continuation-in-part of Ser. No. 08/137,116 filed Jun. 30, 1994, now U.S. Pat. No. 5,500,411 which is national stage application of PCT/EP92/00851 filed Apr. 15, 1992.

FIELD OF THE INVENTION

The subject of the present invention is the use of thrombolytically active proteins for treating thromboembolic conditions, via multiple bolus administration.

The methodology employed inhibits the reocclusion rate in the subject so treated. Preferably, the thrombolytically active protein has a half life longer than that of recombinant wild type t-PA

BACKGROUND AND PRIOR ART

Thrombolytic therapy of myocardial infarction is an effective, medically well tested and proven therapy for the removal of occlusive thrombi in the coronary arteries of the heart. Recombinant human t-PA (tissue-type plasminogen activator) produced by DNA technology in accordance with U.S. Pat. No. 4,766,075 has proven to be effective for the dissolution of coronary thrombi (Verstraete et al., Lancet II, 1985; 965–969). By early lysis therapy of the myocardial infarction the residual heart function after myocardial infarction can be improved in comparison with other therapies (Armstrong et al., J. Am. Coll. Cardiol., 1989; 13: 1469–1476) and a higher survival rate can be achieved in comparison with other therapies (Wilcox et al., Lancet II, 1988; 525–539).

Large thrombolysis studies with, in all, several thousand patients show that rapid induction of thrombolysis with early reperfusion of the myocardial tissue leads to rescue of myocardial tissue and thus to an increase of survival rate (GISSI study group, Lancet I, 1986; 397–401). For this reason, it is necessary to induce thrombolytic therapy at a point of time at which the tissue lying behind the coronary occlusion is not yet irreversibly damaged.

In principle, in the case of the treatment of a coronary occlusion, the problem exists of avoiding reocclusion of the infarcted blood vessel after successful initial thrombolysis. This disadvantageous effect has been observed for recombinant wild type t-PA (e.g., Alteplase) (Cheseboro et al., Circulation, 1987; 76: 142–154). The reocclusion of the infarcted blood vessel leads to increased morbidity and mortality. For the prevention of reocclusions, substances are used of differing pharmacological working principles, such as heparin (Bleich et al., Am. J. Cardiol., 1990; 66: 1412–1417) and acetylsalicylic acid (Hsia et al., N. Engl. J. Med. 1990: 323: 1433–1437). The prolonged infusion of recombinant wild type t-PA (Alteplase) is also said to prevent the reocclusion of the infarcted blood vessel due to a longer period of thrombolysis (Gold et al., Circulation, 1986: 73: 347–352; Verstraete et al., Am. J. Cardiol. 1987; 60: 231–237; Johns et al., Circulation, 1988; 78: 546–556). However, after ending of the infusion, the appearance of reocclusions is frequently observed.

Human tissue plasminogen activator, produced by recombinant DNA technology ("rt-PA") has already been administered as double or multiple boli to a few patients in the scope of clinical preliminary investigations. Admittedly, high dissolution rates of the thrombi were found up to 90 minutes after the administration of the first bolus but, because of the high doses, extensive, systemic plasminogen activation with subsequent almost complete reduction of fibrinogen was observed (only 15.5 to 5.2% of the initial value) (J. Am. Coll. Cardiol. 1991 (17(2), 152A). Undesired reduction of fibrinogen levels represents a disadvantage in that during emergency operations, since there is a high tendency to hemorrhage, intensive supervision of the patient is necessary. Further, in the case of double and triple bolus administration of rt-PA, a tendency to reocclude was observed in the blood vessels (Circulation, 1990, 82(4), Suppl. III, 538, abstract 2137; Br. J. Haematol. 1991, 77, Suppl. 1, 47, abstract P080). A study was also carried out for Alteplase in which multiple bolus administration was investigated in more detail (Coronary Artery Disease, 1990, 1(1), 83–88). The study concluded that single bolus administration was preferred.

Because of the above-mentioned disadvantageous effects, administration of rt-PA in the form of a double or multiple bolus has found no practical use. Furthermore, the bolus administration of rt-PA has been regarded as being inexpedient from the fact that the half life of rt-PA is relatively short and only amounts to 3–6 minutes (Garabedian et al., J. Am. Coll. Cardiol. 1987; 9: 599–607). This means that, to ensure thrombolytic efficacy, relatively long-lasting infusion is necessary for the maintenance of effective plasma levels. However, in emergency situations the long-lasting infusion of r-tPA (30 minutes to 6 hours) represents a distinct treatment disadvantage. Furthermore, this leads to increased risk of hemorrhages (Marder and Sherry, N. Engl. J. Med. 1988; 318: 1512–1520).

surprisingly, it has now been found that thrombolytically active proteins, preferably those with a half life longer than that of rt-PA can be used successfully in the treatment of coronary occlusions, when the proteins used are administered in the form of a fractionated administration of two or more bolus injections. Also, all thrombolytically active proteins, when combined with heparin can be used in the multiple bolus system described herein. In this way, rapid and simple administration of thrombolytically active proteins for the effective treatment of thromboembolic diseases by, e.g., inhibiting reocclusion rate, is made possible.

KU/kg of BM 06.022, at time point t=0 minutes. Data are shown in mean values ±SEM, where four dogs were used in each group. "Pre" indicates initial blood flow.

Figure 3:
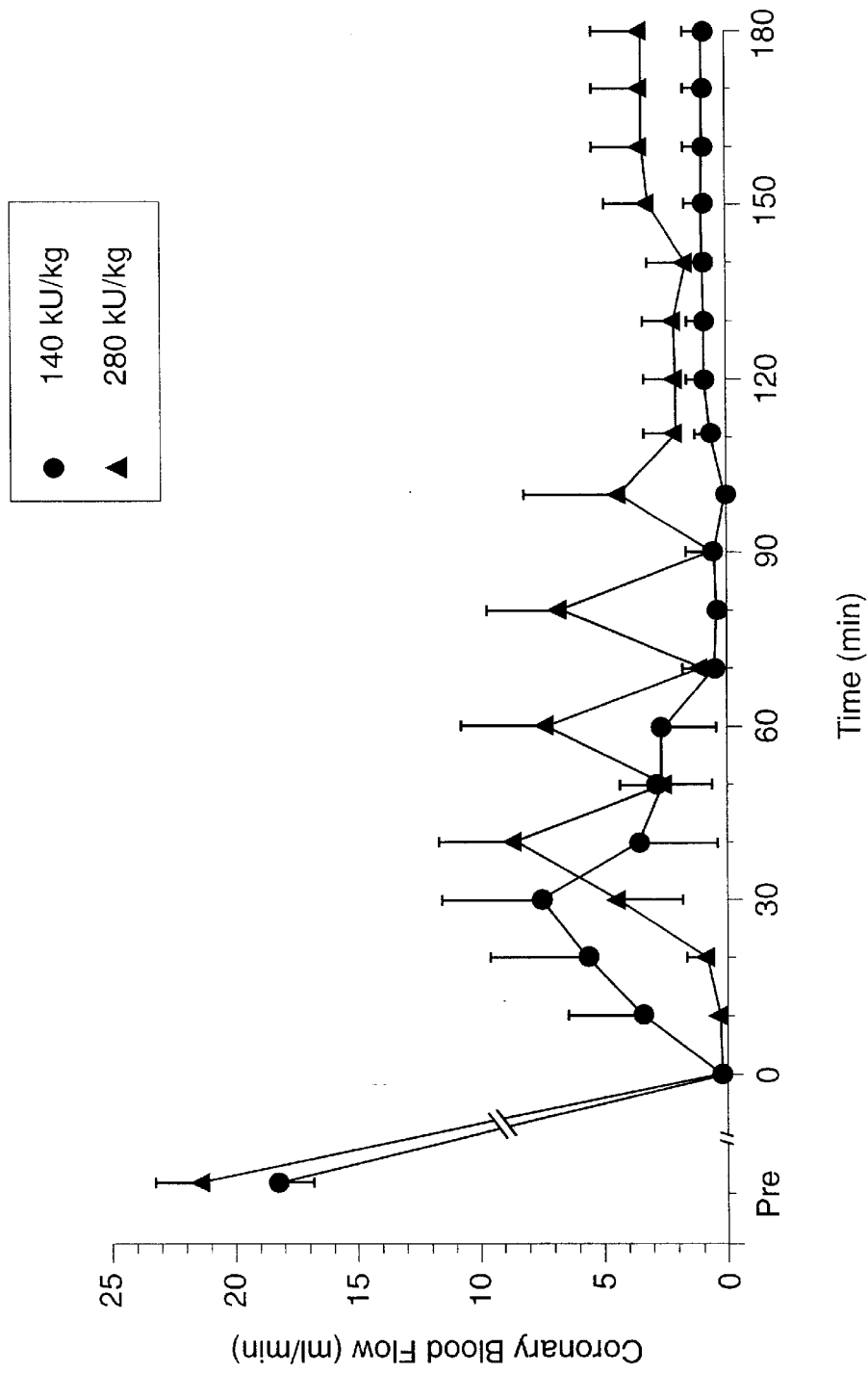
FIG. 3 displays time course of coronary blood flow after a single intravenous bolus injection, using either 140 or 280
Figure 4:
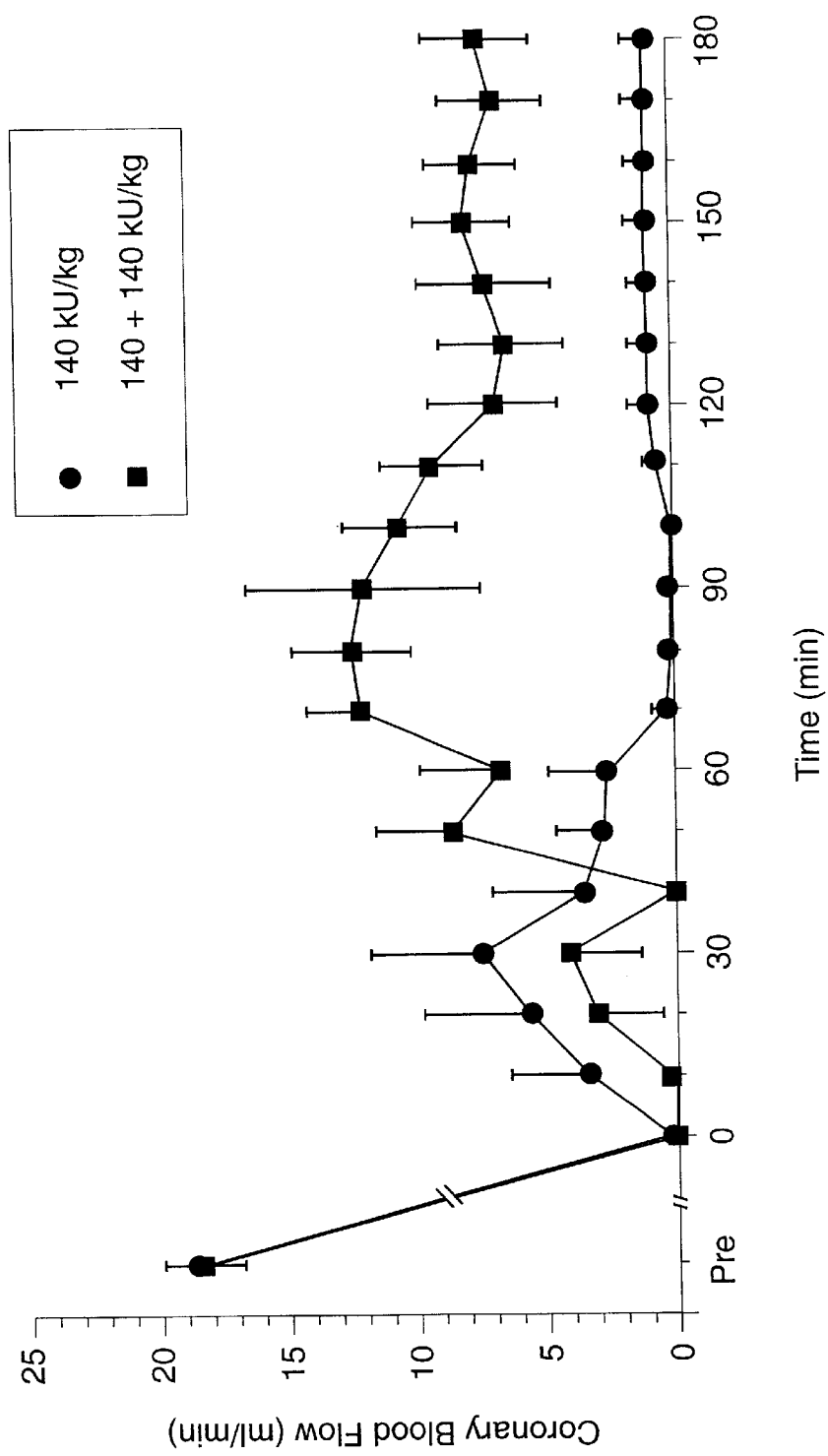

FIG. 4 also shows time course of coronary blood flow as in FIG. 3, (single bolus, t=0), and double bolus (140 KU/kg each bolus, at t=0 and t=44 minutes).

Figure 5:
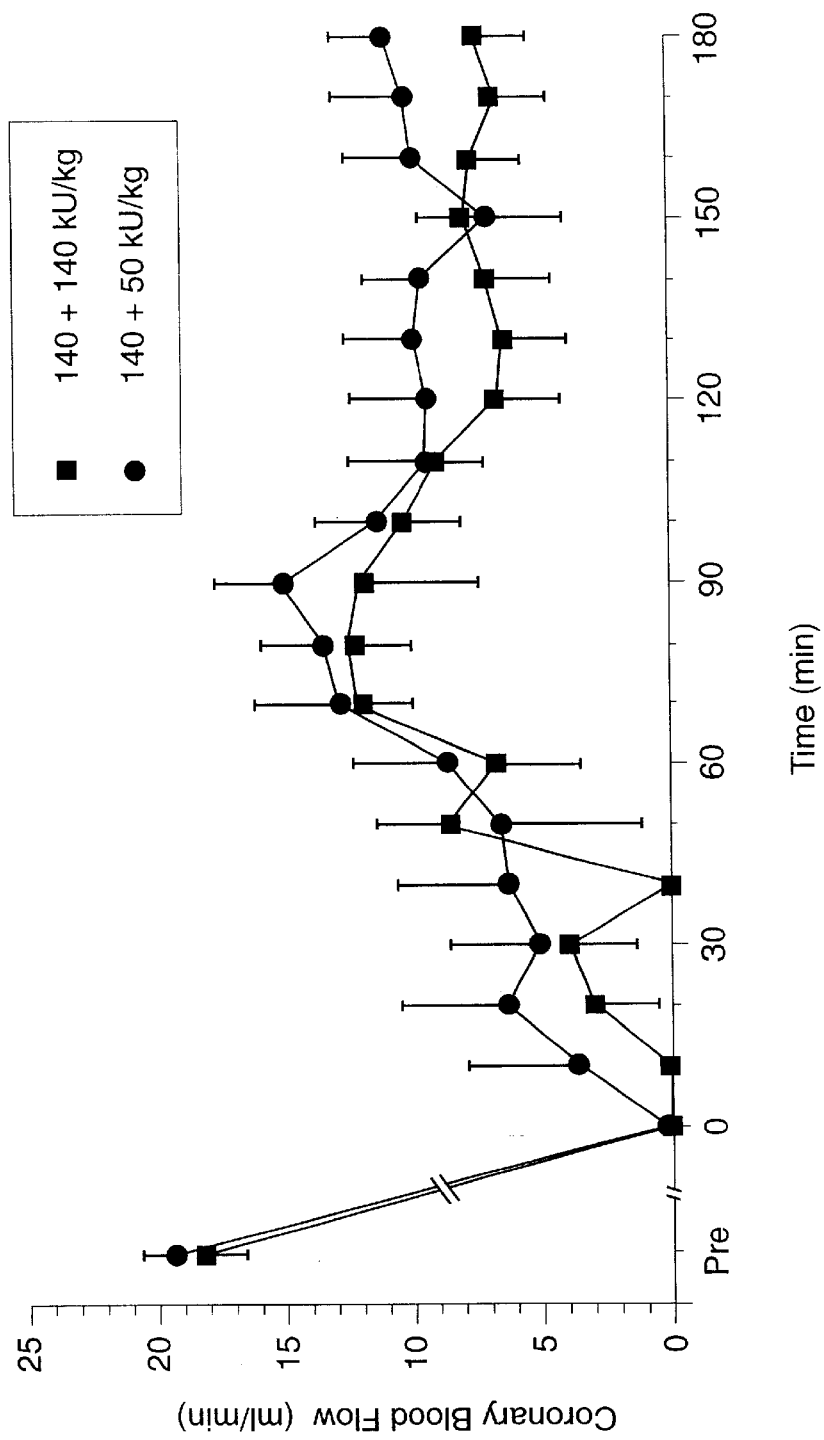

FIG. 5 shows time course of coronary blood flow before and after double bolus administration (140 KU/kg each bolus, for six dogs), or of 140 and 50 KU/kg administrations (for five dogs), of BM 06.022 in both cases, again at t=0 and t=44 minutes. Data are calculated and presented as explained in FIG. 3.

Figure 6:
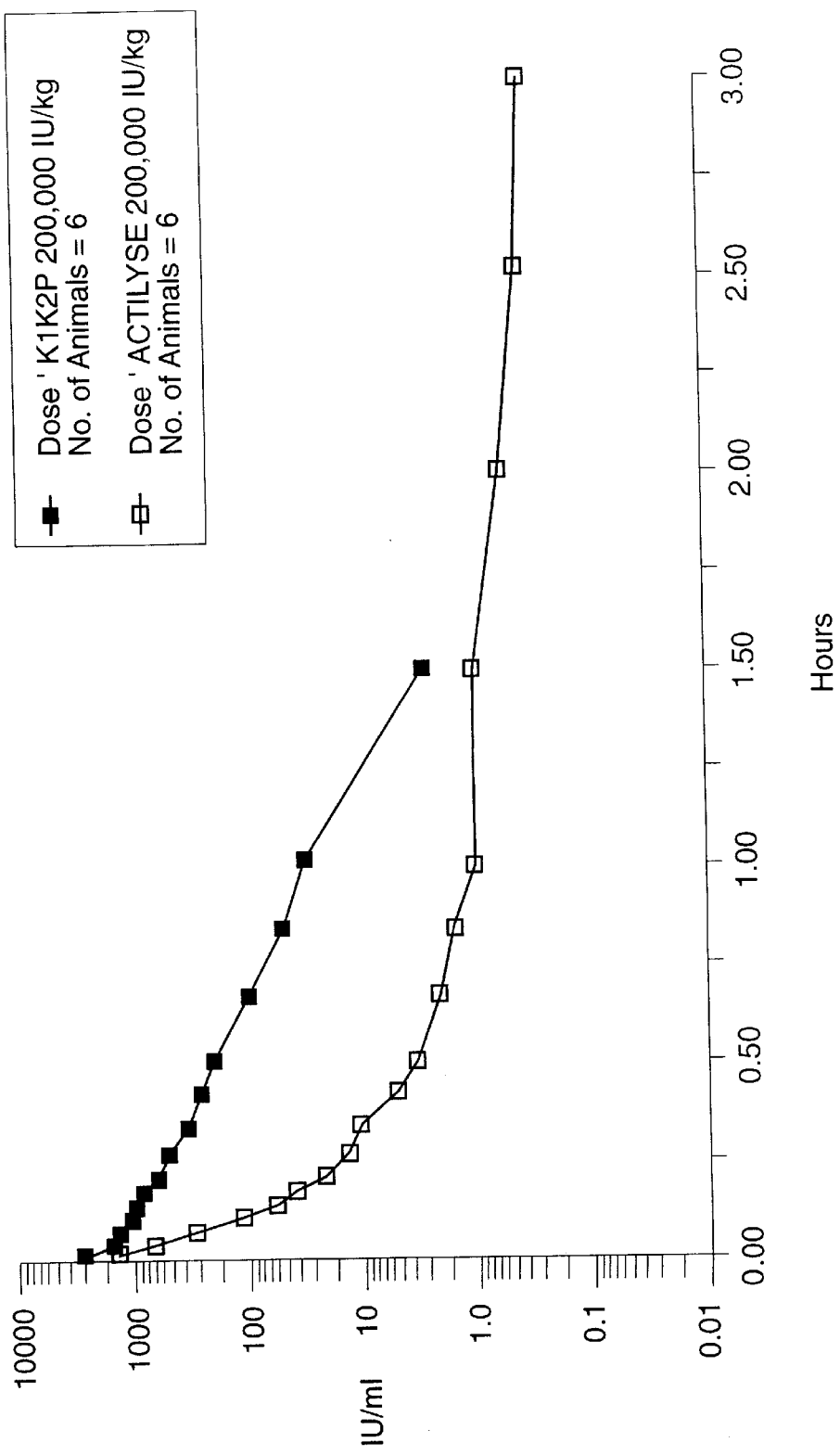

FIG. 6 compares plasma concentration time curves of thrombolytic protein K1K2P and wild type t-PA.

Figure 7:
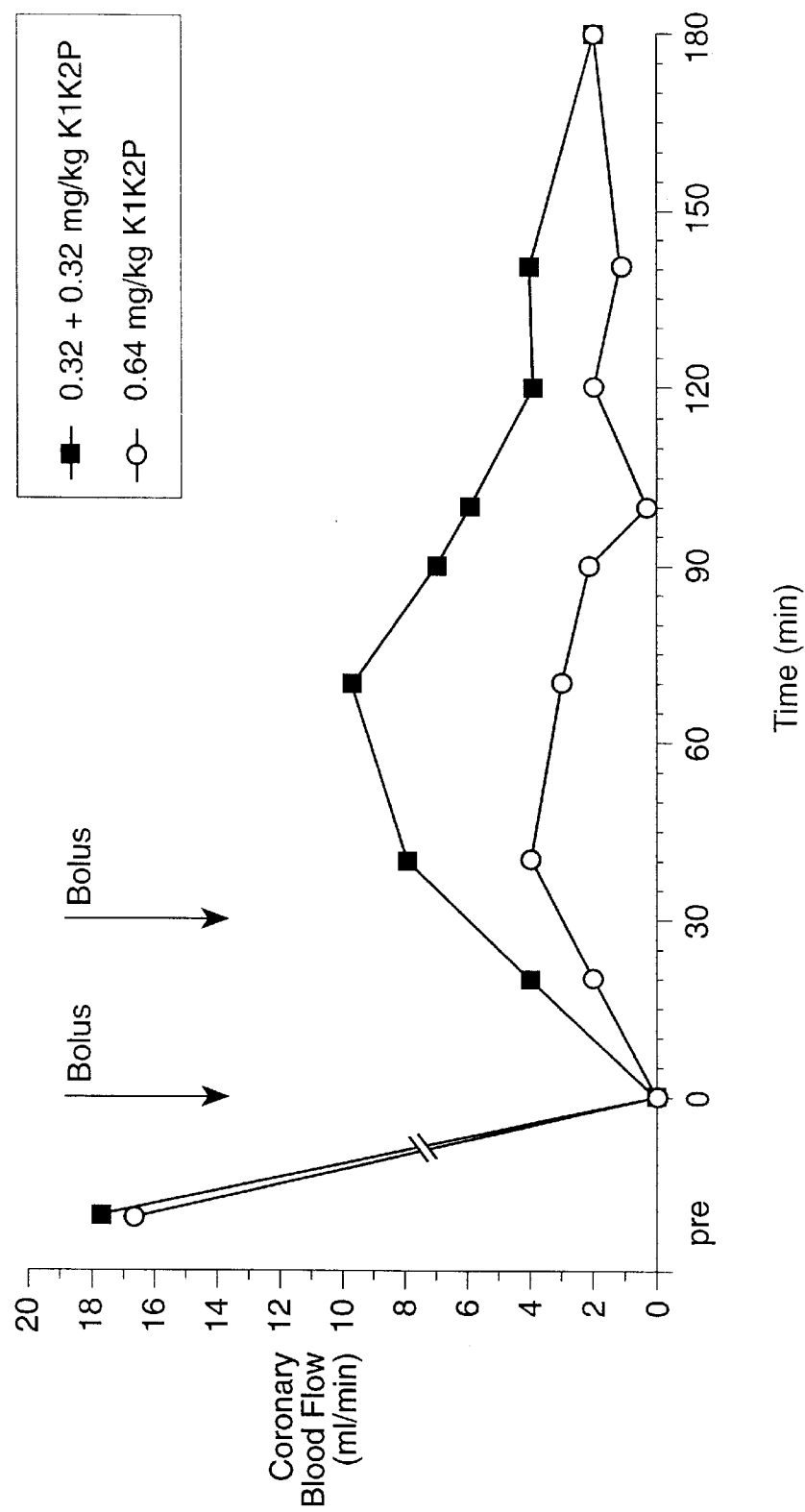

FIG. 7 compares double bolus and single bolus administration of K1K2P.

Figure 8:
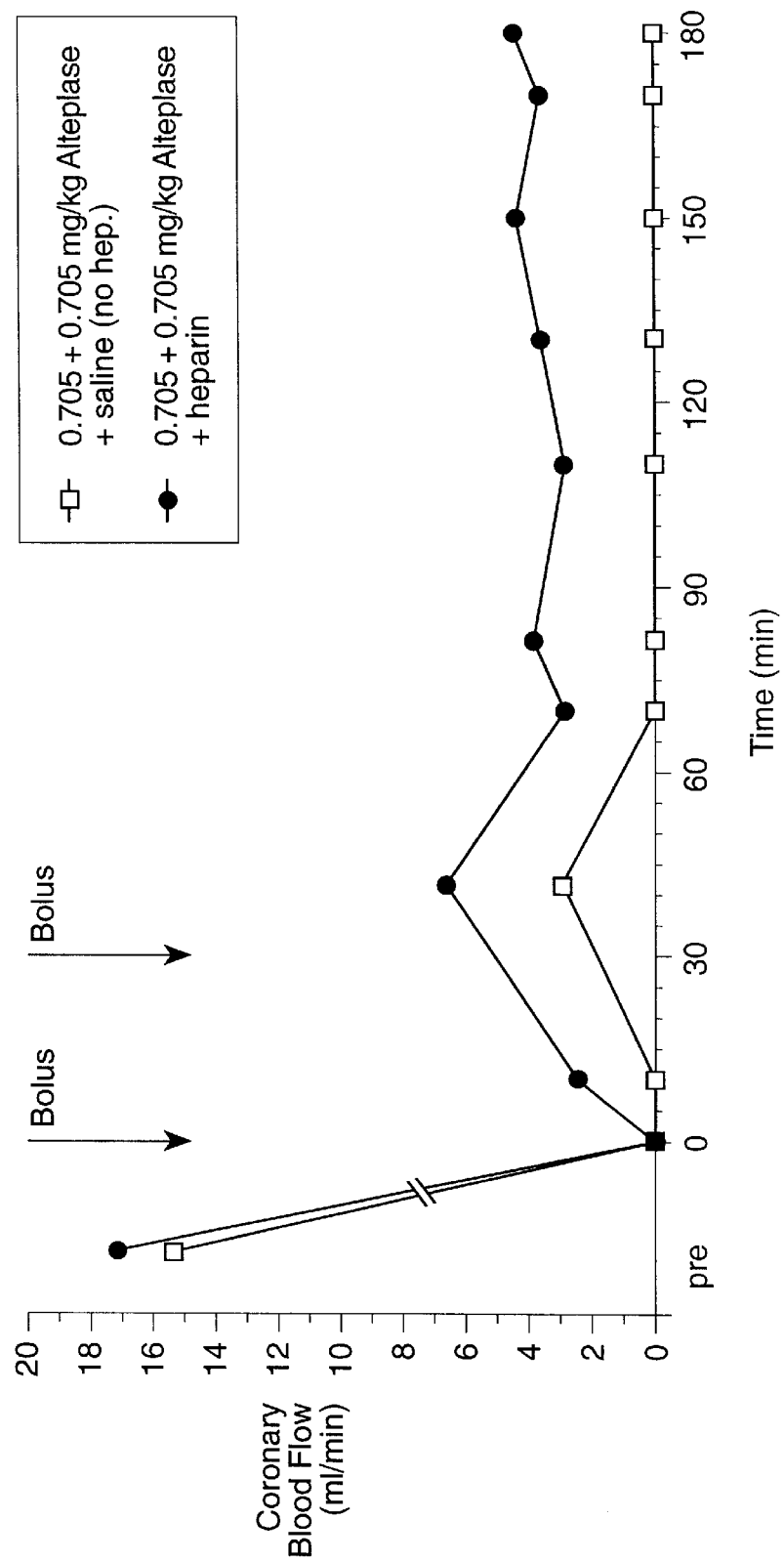

FIG. 8 compares reperfusion results obtained when wild type t-PA with or without heparin.

DETAILED DESCRIPTION OF PREFERRED EMBODIMENTS

In the present invention, the term "fractionated administration" means the administration of a therapeutically effective amount of a thrombolytically active protein in two or more partial amounts in the form of a double or multiple bolus, "therapeutically effective amount" referring to sufficient protein to inhibit reocclusion.

Bolus administration is an intravenous rapid injection and is, therefore, especially advantageous because the time from the beginning of the clinical symptoms up to treatment and, also the time from the commencement of treatment up to the dissolving of the coronary thrombus is shortened. Thus, more myocardial tissue can be rescued from irreversible destruction. The double or multiple bolus administration according to the invention brings about a higher thrombolytic potency of the thrombolytically active protein used. In this way, it is possible to reduce dosages as compared to rt-PA. Multiple bolus means that the injections are all completed over the course of a 24 hour day. During acute treatment, they are made at four hour intervals. Other preferred regimes are described infra. Surprisingly, after bolus injection, more rapid reperfusion as compared to administration in the form of an infusion is found. Furthermore, double or multiple bolus administration brings about a significant prolongation of the cumulative patency time (sum of the time intervals after reperfusion in which coronary blood flow is present), as well as a distinct increase of coronary blood flow, as well as increased o stability at a relatively high level for a longer period of time after the administration. Furthermore, double or multiple bolus injection has the surprising advantage of a smaller decrease of plasma fibrinogen as compared to single bolus injection. However, these advantageous properties are not achieved with administration of the corresponding total amount of the thrombolytically active protein by single bolus injection.

Thromboembolic conditions in the meaning of the present invention include, but are not limited to, those diseases which are attributable to myocardial infarction or to reocclusion of the coronary arteries. Reocclusions occur quite frequently as a result of the use of thrombolytic agents for the treatment of heart infarcts. The cause of myocardial infarctions is the formation of a thrombus in the coronary arteries. This thrombus consists of a combination of fibrin and thrombocytes. The primary aim in treatment of heart infarcts is the rapid dissolution of this thrombus and the recreation of the blood flow (reperfusion). Successful therapy must dissolve the thrombus as quickly as possible and prevent its reformation (reocclusion). Double or multiple bolus administration in accordance with the present invention is especially advantageous for the treatment of brain stroke.

Pharmaceutical packaging units prepared for use in the invention consist of a form of administration which contains the thrombolytically active protein or the protein plus heparin, instructions, for example in the form of a package leaflet prescribed for medicaments, from which it follows that the administration of a therapeutically effective amount of the medicament advantageously takes place by double or multiple bolus administration. The information regarding the manner of the use can also be given as a packaging overprint on the medical preparation already, or can be taken from an information leaflet which can be brought together with medicinal preparations which contain thrombolytically active proteins. As suitable forms of administration for thrombolytically active proteins, galenical formulations, for example lyophilisates or solutions in appropriate containers, such as e.g., in ampules are, preferred. As a rule, these formulations contain usual pharmaceutical adjuvants which are suitable for the preparation of isotonic solutions, and may also include additional stabilizing and solubilizing agents.

Thrombolytically active proteins which, in comparison with rt-PA possess a prolonged half life time, are preferred. These proteins bring about dissolution of thrombi and bring about reperfusion through blood vessels. As already mentioned above, the half life of rt-PA in human blood is about 3–6 minutes.

In accordance with the invention, it is preferred to use thrombolytically active proteins which have a half life at least twice that of rt-PA. In particular, those thrombolytically active proteins which have half lives 3–30 times that of rt-PA are preferred. More particularly, the agent should have a half life 3–7 times, and more preferably 3–5 times that of rt-PA. In terms of minutes, the thrombolytically active proteins should have half lives of from at least about 10 minutes to about 90 minutes, preferably at least about 10 to about 40 minutes, and more preferably about 10–20 minutes. When used in combination with heparin, thrombolytically active proteins which do not have a longer half life than rt-PA can be used, as well as thromobolytically active proteins of the type discussed supra.

In the meaning of the present invention, thrombolytically active proteins include, e.g., LY 210825 (K2P from Syrian hamster cell lines, Circ. 1990, 82, 930–940); ΔFE3x and ΔFE1x (K1K2P from Chinese hamster ovary cells, Blood, 1988, 71, 216–219); ΔFEK1 (K2P from mouse C127 cells, J. Cardiovasc. Pharmacol. 1990, 16, 197–209); E-6010 (Jap. Circ. J. 1989, 53, p. 918); t-PA variants (Thromb. Haemost., 1989, 62, p. 542); K2P and D-K2P (Thromb. Haemost., 1989, 62, p. 393); MB-1018 (FK2K2P, Thromb. Haemost., 1989, 62, p. 543); FK2P (FASEB J., 1989, 3, A1031, abstract 4791); Δ1x (Circulation, 1988, 4, II-15); K1K2P (Thromb. es., 1988, 50, 33–41); FK1K2P (J. Biol. Chem., 1988, 263, 1599–1602). Especially preferred are thrombolytically active proteins which consists essentially of the K2 ("Kringle 2"), and serine protease ("P") domains of human t-PA. Especially preferred is the thrombolytically active protein of U.S. Pat. No. 5,223,256, the disclosure of which is incorporated by reference. Other proteins of this kind are described in the following references:

U.S. Pat. No. 4,970,159; EP-A-0,207,589; AU 61804/86; EP-A-0,231,624; EP-A-0,289,508; JP 63133988; EP-A-0,234,051; EP-A-0,263,172; EP-A-0,241,208; EP-A-0,292,009; EP-A-0,297,066; EP-A-0,302,456; EP-A-0,379,890.

In the case of such thrombolytically active proteins with prolonged half life, the pharamcokinetic profile differs from rt-PA. The determination of the half life takes place according to the processes known from the prior art (Pharmacokinetics, Ch. 2, Marcel Dekker, New York 1982).

Preferred thrombolytically active proteins include molecules produced by recombinant DNA technology which contain the regions of the natural protein human t-PA responsible for thrombolysis. Those proteins can be used which display deletions or substitutions of individual or several amino acids in the sequence of the molecule as long as the half life of such derivatives is prolonged with regard to rt-PA in the manner described above. Preferred are derivatives which consist essentially of the K2 and P domains of t-PA, or those which contain amino acids 1–5 and 88–527 of natural t-PA. These derivatives are referred to as "K1K2P" hereafter.

By way of example for the present invention, thrombolytically active protein K2P (BM 06.022) is described in more detail in U.S. Pat. No. 5,223,256, the disclosure of which is incorporated by reference. It consists essentially of the kringle 2(K2) and protease (P) domains of human t-PA and, because of its expression in *Escherichia coli* cells, is unglycosylated. The specific activity of K2P is 550±200 KU/mg. K2P is used for the thrombolytic therapy of thromboembolic disease, such as myocardial infarction, lung embolism, stroke and other occlusive vessel diseases. Also useful is the protein K1K2P, which contains only amino acids 88–257 of wild type t-PA (see, e.g., U.S. Pat. No. 4,766,075 for the sequence).

Due to lack of glycosylation, reduced clearance, and a half life which is at least 3–4 times greater than that of t-PA results. The thrombolytic effect of the bolus administration of K2P, and others, was investigated in various animal models. These showed a thrombolytic effectiveness increase of approximately 5 compared with rt-PA. Especially impressive was the rapid opening of thrombolytically occluded vessels, in comparison with rt-PA and other thrombolytics, which means a reduced time for the blood vessel opening in comparison with other thrombolytics and thus a more rapid reperfusion of the infarcted myocardial tissue.

On the basis of the improved pharmacokinetic properties of K2P, e.g., the effective dose to be administered can be reduced and K2P can be administered as i.v. multiple bolus injections. A very rapid maximum reperfusion is achieved. Furthermore, by the administration of double or multiple boli, the impairment of perfusion in the coronary arteries after reperfusion (tendency to reocclude) is significantly reduced or prevented. In addition, after double or multiple boli, the decrease of plasma fibrinogen is smaller than after the single bolus injection of the same total dose.

Besides the rapid opening of thrombolytically occluded blood vessels, the inhibition of the reocclusion of the opened blood vessels is of great clinical importance since a reocclusion of the infarcted blood vessel can lead to clinically important reinfarction with clinical complications resulting therefrom.

The administration of the protein as a bolus in equieffective doses in comparison to the infusion of rt-PA leads, in the animal model, to a surprisingly rapid opening of infarcted blood vessels and thus makes possible a rapid reperfusion of infarcted myocardial tissue. In view of the present knowledge regarding thrombolysis, this observed effect is to be evaluated very positively from the clinical point of view.

The time integral between beginning of the first and subsequent bolus injection is indication-dependent and can amount to between 10–90 minutes, 30–90 minutes being specially preferred. The injection period is itself relatively short and amounts, depending upon the volume to be administered, to about 0.5–3 minutes, with an injection rate of about 5–10 ml/min being especially advantageous.

"Multiple bolus administration" refers, e.g., to the cumulated administration of two or more individual bolus injections which are administered over an interval of time, i.e., one day. Two or more, preferably three, bolus injections are carried out daily, whereby the therapy can extend over the course of several successive days. This treatment scheme can be interrupted by one or two days so that administration in the form of bolus injections can take place, for example, on every second day during the whole treatment period. Essentially, this cumulated administration of single boli differs from the known single bolus administration in that the administration is repeated daily several times. If the time interval between the first and a subsequently following bolus injection is relatively short, about 10 minutes up to one hour, one speaks of a double bolus or multiple bolus administration. If the time intervals are of the order of magnitude of several hours, then one can also speak of a cumulated administration of single boli.

For the production of the pharmaceutical forms of administration with regard to the thrombolytically active protein, the usual pharmaceutical adjuvants and additive materials can be O used. Furthermore, stabilizing or solubilizing agents, such as basic amino acids (arginine, lysine or ornithine) can be used. Suitable galenical forms of administration are known from the prior art or can be produced according to the generally usual methods (cf. U.S. Pat. No. 4,477,043; EP 0,228,862; WO91/08763; WO91/08764; WO91/08765; WO91/08766; WO91/08767 or WO90/01334). The material can be administered in lyophilized form or as an injection solution, ready for use. The bolus injection can take place intravenously, intramuscularly or also subcutaneously. Intravenous injection is preferred.

The amount of the thrombolytically active protein can be the same or also different in the boli, depending upon the particular requirements. As a rule, amounts of 3–50 MU per container are used, corresponding to approximately 5–90 mg of protein. A larger amount of the protein is preferably administered with the first bolus than for the second bolus injection. In particular, amounts of 5–20 MU, especially of 5–15 MU, are used for the first and 3–25 MU, especially 3–10 MU for the second bolus injection. It is especially preferred to use about 10 MU for the first and about 5 or 10 MU for the second injection. The cumulative dose preferably lies in the range of 15–40 MU.

The invention is explained in more detail on the basis of the following examples.

EXAMPLE 1

For the experiments, a dog model was used for the simulation of myocardial infarction. Adult beagles of both sexes were narcotized with barbiturates, intubated and artificially respirated. Arterial and venous catheters were applied in order to monitor the blood pressure, to administer substances or to take blood samples. The chest was opened and the heart exposed. A short segment of the ramus circumflexes of the arteria coronaria sinistra was isolated and prepared. Subsequently, the coronary artery was provided with the following instruments in proximal to distal direction: an electromagnetic flow probe for the measurement of the blood flow in the coronary artery, a stimulation electrode, an adjustable screw and a thread. The tip of the stimulation electrode was passed through the wall of the coronary artery and so placed within the blood vessel that the needle tip came into contact with the inner surface of the blood vessel. The screw was adjusted so that 90% of the reactive hyperemia were eliminated as the result of a short-term interruption of perfusion of the coronary artery.

A thrombus in the coronary artery was formed according to the method originally described in Romson et al. (Thromb. Res., 1980; 17: 841–853) in order to initiate myocardial infarction. The method was employed in the modified form of Shebuski et al. (J. Pharmacol. Exp. Ther. 1988; 246: 790–796). Via the stimulation electrode, a 150 microampere direct current was applied to the coronary artery and maintained until the blood flow in the coronary artery fell to 0 ml/min and remained there for at least three minutes. Subsequently, the thrombus should age for 30 minutes. Over this time period, and over the remainder of the experiment, the animals were heparinized at a dosage of 1000 units/animal/hour. Thirty minutes after thrombus formation, the thrombolytic protein or a solvent was administered as a one-minute i.v. bolus injection to six animals per group. BM 06.022 was administered in four doses: 50, 100, 140 and 200 KU/kg. rt-PA was also given in four doses: 200, 800, 1130 and 1600 KU/kg (=2 mg/kg). The specific activity of rt-PA was 800,000 IU/mg (=800 KU/mg). Plasma samples were obtained before and again after injection of the thrombolytic in order to determine the concentration of the activity of BM 06.022 or of rt-PA according to the method of Verheijen et al. (Thromb. Haemostas. 1982; 48: 266–269). Reperfusion was assumed if at least 33% of the initial blood flow in the coronary artery was again achieved. Accordingly, the time to reperfusion from the beginning of the injection up to the achievement of this blood was defined. In each animal in an additional experimental group, BM 0 06.022 was administered in a dosage of 140 KU/kg and t-PA in a dosage of 800 KU/kg (=1 mg/kg) intravenously over 90 minutes as continuous infusion (10% of the total dosage as initial i.v. bolus).

Figure 1:
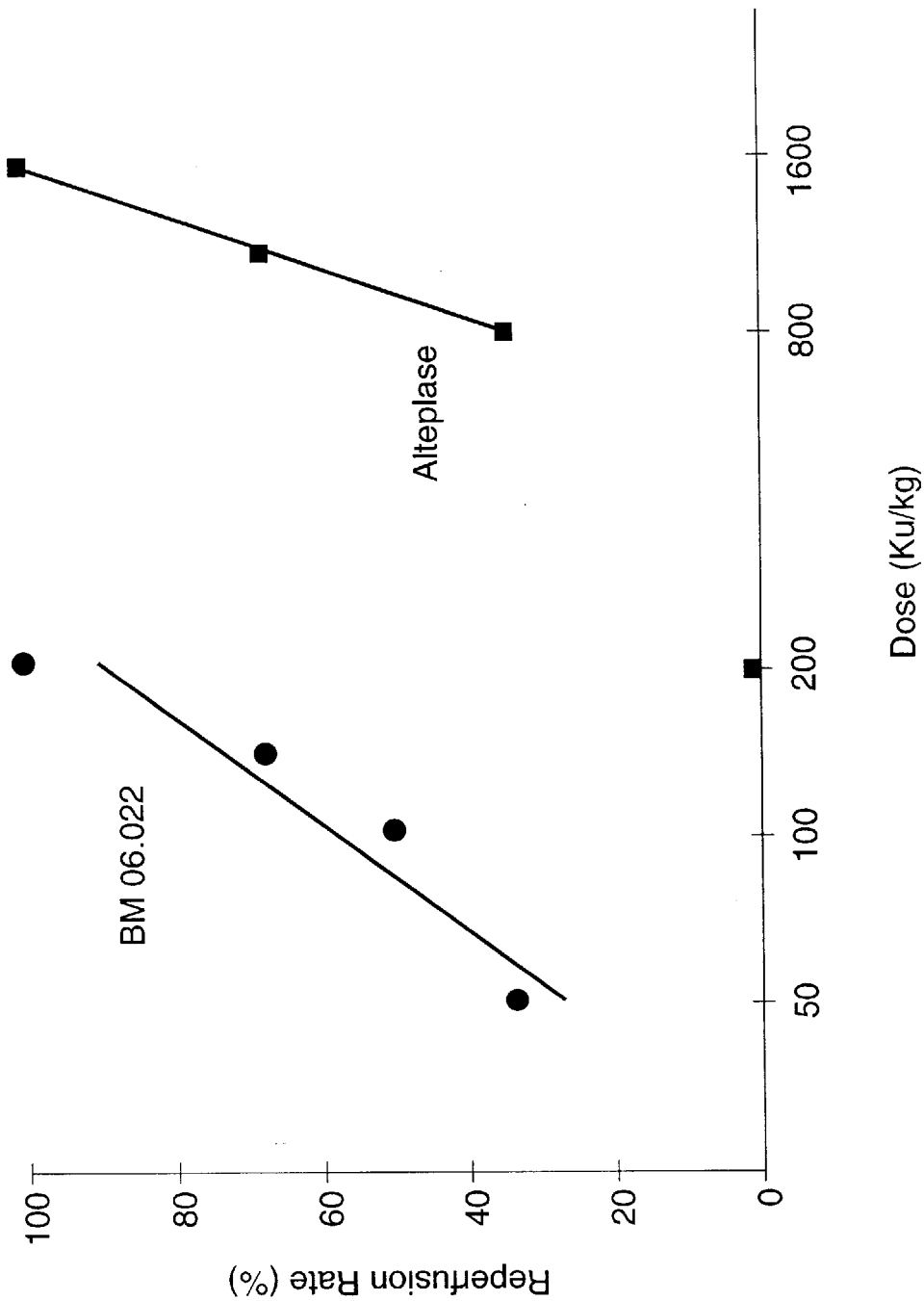
FIG. 1 compares the thrombolytic dose-effect range of thrombolytically active protein BM 06.022 and r-tPA (Alteplase), following an intravenous injection extending over one minute, in a dog model where the animals have coronary thrombosis. Reperfusion rate (%) is given as the percent of reperfused dogs with a dosage group (each group contains 6 dogs). The curves were produced using semi-logarithmic regression analysis.
Figure 2:
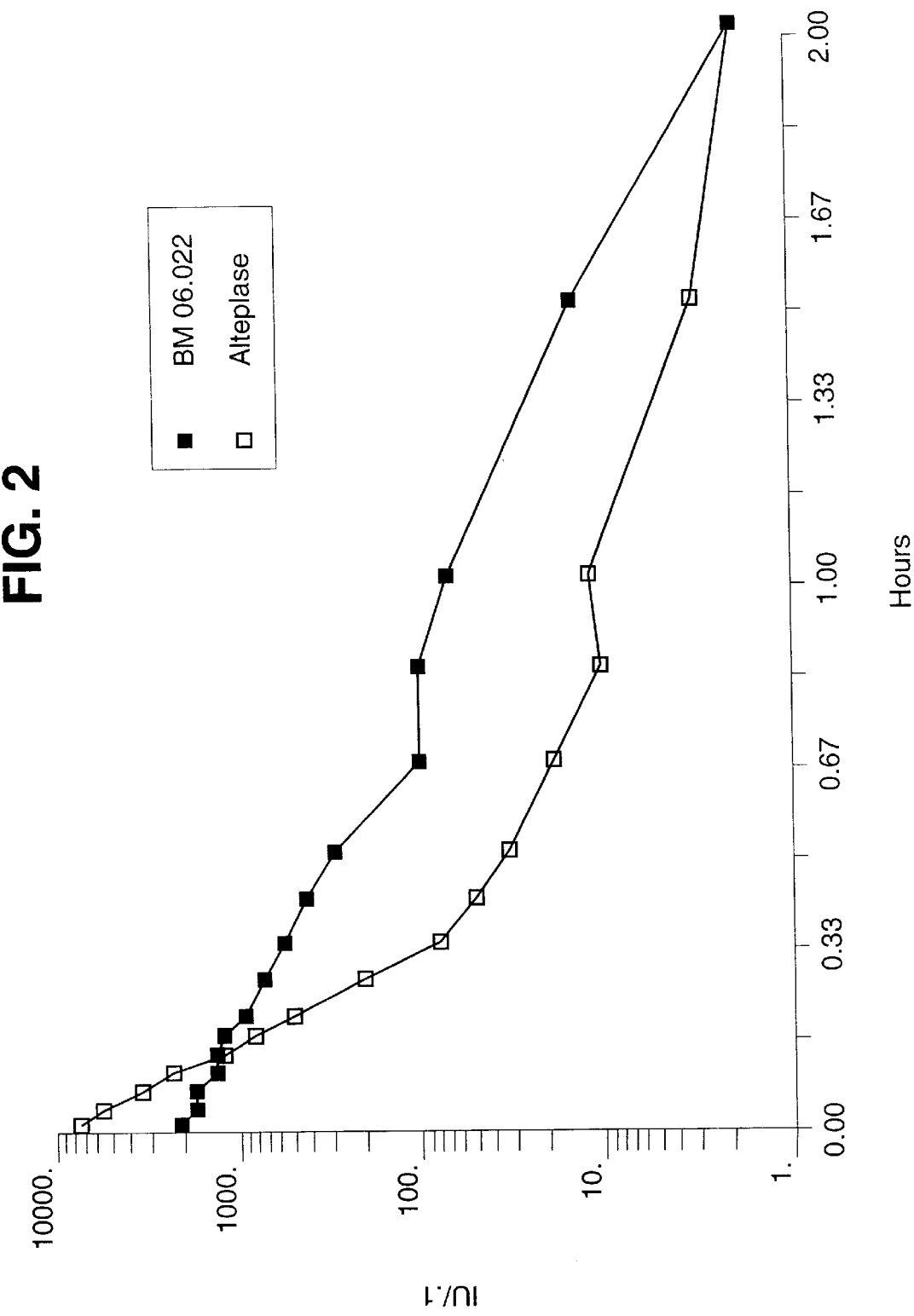
FIG. 2 compares plasma concentration time curves, pharmacokinetically, using BM 06.022 and rt-PA "Alteplase" in anesthetized dogs. 140 KU/kg (1 mg/kg) of either Alteplase or BM 06.022 were used, in groups of six dogs. What is presented is the arithmetic mean value. Starting concentration was subtracted from subsequent measurements.

FIG. 1 shows the dose-effect relationship for the reperfusion rate after bolus injection of BM 06.022 or of rt-PA. 100% reperfusion (6 out of 6 animals) was achieved with i.v. bolus injection of 200 KU/kg in the case of BM 06.022. In the case of the same dose of rt-PA, none of the animals reperfused. For the achievement of the same maximum effect, an injection of 1600 KU/kg (=2mg/kg) of rt-PA was necessary. This injection dose is approximately twice as high as the dose of rt-PA presently used in the clinic as infusion (about 1 mg/kg). The higher thrombolytic potency of BM 06.022, as seen by the shift to the left of the dose effect curve, can be explained by the improved phamacokinetic properties of BM 06.022 (see FIG. 2). The total plasma clearance of BM 06.022 amounts to 4.4±0.4 and that of rt-PA to 20.4±2.0 ml/min⁻1/kg⁻¹. Thus the total plasma clearance (a measure of the removal of a substance from the plasma) of BM 06.022 is about 4.6 times slower than that of rt-PA. Furthermore, it was found that rt-PA, after infusion, achieves twice as high a reperfusion rate than after single bolus injection of the same dose (800 KU/kg). BM 06.022 in a dose of 140 KU/kg shows the same reperfusion (4 out of 6 animals) after injection and after infusion but the time to reperfusion was significantly shorter than injection (Table 1).

The results show that rt-PA displays more favorable thrombolytic success after infusion than after injection. This finding agrees with the clinical practice in which rt-PA is usually administered as an infusion (Cheseboro e a., Circulation, 1987; 76: 142–254). The slower elimination of BM 06.022 from the plasma as compared to rt-PA led to a higher thrombolytic potency of BM 06.022. Not only is dosage reduction thereby possible but, after single i.v. bolus injection, surprisingly, a more rapid reperfusion takes place than after infusion.

TABLE 1

Coronary thrombolytic properties of Alteplase and BM 06.022

| | dose (kU/kg) | reperfusion rate | time to reperfusion (min) | reocclusion rate | time to reoclusion (min) |
|---|---|---|---|---|---|
| Alteplase bolus injection | 800 | 2/6 | 35 | 1/2 | 4 |
| Alteplase infusion | 800 | 4/6 | 18 ± 8 | 4/4 | 7.8 ± 4.1 |
| BM 06.022 bolus injection | 140 | 4/6 | 15 ± 6 | 4/4 | 9.3 ± 5.3 |
| BM 06.022 infusion | 140 | 4/6 | 59 ± 12⁺ | 4/4 | 3 ± 0.4 |

The data represent average values ±SEM; n=6 per group +<0.05 vs. BM 06.022 injection group by means of Mann-Whitney test.

EXAMPLE 2

For the experiments described herein, the same dog model of coronary artery thrombosis as in Example 1 was used. However, in contrast to the experiments in Example 1, the thrombus was aged for one hour instead of only 30 minutes. BM 06.022, i.e. "K2P" was administered either as a single i.v. bolus administration, or the first bolus dose amounted to 140 KU/kg, followed by the second bolus in a dose of 140 or 50 KU/kg of BM 06.022. (44 minutes later). Each of the four experimental group consists of six dogs. Additional parameters for the evaluation were the maximal coronary blood flow which was measured after reperfusion and the coronary blood flow at termination of the experiment three hours after injection. Furthermore, the cumulative patency time was calculated, i.e., the sum of the time intervals after reperfusion in which coronary blood flow was present. The animal model is so designed that, typically, after reperfusion, cyclic flow variations occur with reocclusion. At the end of the experiment, the residual thrombus was removed and its wet weight measured.

In both groups with single bolus injection, four of six animals reperfused. In the double bolus group, six of six or five of six animals reperfused (Table 2). The results shown in Table 3 for the cumulative patency time, the coronary blood flow and the residual thrombus weight show that double bolus administration of BM 06.022 significantly increased the coronary blood flow which also remains significantly increased at the end of the experiment, and the residual thrombus weight has decreased significantly in comparison with the single bolus injection of 140 KU/kg. FIG. 3 shows that an increase of the single bolus injection from 140 to 280 KU/kg did not markedly improve the coronary blood flow. Strongly cyclic flow variations were still observed. On the other hand, in FIG. 4 it can be seen that the double bolus administration of 140 and 140 KU/kg of BM 06.022 clearly improved the coronary blood flow in comparison with the single bolus injection of 140 KU/kg of BM 06.022. The same effect on the coronary blood can also be achieved by the double bolus administration of 140 and 50 KU/kg of BM 06.022 (FIG. 5). As Table 4 shows, dividing up a total dose of 280 KU/kg into 140 and 140 KU/kg instead of the single bolus injection of the same total dose of BM 06.022 prevents the significant decrease of the plasma fibroinogen observed previously.

TABLE 2

Reperfusion characteristics on BM 06.022-treated dogs

| BM 06.022 dose (kU/kg) | reperfusion rate (reperfulsed/all) in all | after the 2nd bolus | time after the 1st bolus | to reperfusion (min) after the 2nd bolus |
|---|---|---|---|---|
| 140 | 4/6 | — | 18.3 ± 6.0 | — |
| 280 | 4/6 | — | 26.5 ± 4.9 | — |
| 140 + 140 | 6/6 | 2/6 | 21.8 ± 4.4 | 16.0, 4.0 |
| 140 + 50 | 5/6 | 1/6 | 18.3 ± 4.1 | 8.0 |

The data represent mean values ±SEM or frequency data 1st bolus: t=0–1 min; 2nd bolus: t=44–45 min.

TABLE 3

Characteristics of the coronary blood flow after reperfusion and thrombus weight in BM 06.022-treated dogs

| BM 06.022 dosing (kU/mg) | N | cumulative patency time (min) | coronary blood flow (ml/min) maximum | at 3 h | residual thrombus moist wet (mg) |
|---|---|---|---|---|---|
| 140 | 4 | 47.5 ± 13.1 | 12.5 ± 3.2 | 0.8 ± 0.8 | 6.1 ± 1.1 |
| 280 | 4 | 80.8 ± 34.1 | 11.8 ± 1.8 | 3.3 ± 1.9 | 3.5 ± 0.8+ |
| 140 + 140 | 6 | 121.5 ± 11.2+ | 19.3 ± 1.5+ | 6.8 ± 1.8+ | 2.4 ± 0.8+ |
| 140 + 50 | 5 | 127.4 ± 10.3+ | 21.2 ± 2.2+ | 8.4 ± 1.7+ | 3.4 ± 0.5+ | the data represent the mean value ±SEM; n=6/group for the thrombus weight.

Cumulative patency time: sum of the time intervals in which the coronary artery was open (determined) via measurement of the coronary blood flow)+p<0.05 vs. the 140 kU/kg BM 06.022 group by means of Student's t-test.

TABLE 4

Coagulation variables in BM 06.022-treated dogs

| BM 06.022 dose (kU/kg) | residual fibrinogen (% of the initial value) | residual plasminogen (% of the initial value) | residual $\alpha_2$-antiplasmin (% of the initial value) |
|---|---|---|---|
| 140 | 95.7 ± 3.7 | 90.7 ± 3.6 | 52.2 ± 6.5 |
| 280 | 74.0 ± 9.4+ | 76.0 ± 2.4+ | 54.5 ± 19.3 |
| 140 + 140 | 97.5 ± 6.0 | 82.5 ± 2.4+ | 60.2 ± 7.5 |
| 140 + 50 | 94.9 ± 3.5 | 82.6 ± 2.9 | 62.0 ± 14.1 |

The data represent the mean value n=6/group.

The coagulation variables are represented as the 2-hour percentage values of the initial value +p<0.05 vs. the 140 kU/kg 06.022 group by means of Student's t-test.

The results show that the deterioration of the coronary blood flow after reperfusion, which, in this model, intrinsically occurs in simulation of patients with reocclusion tendency, cannot be prevented by single bolus injection, even at higher dosages. On the other hand, the administration of the double bolus is surprisingly able to prolong the cumulative patency time, to increase the blood flow quantitatively and to maintain the increased flow up to the end of the experiment. In addition, the double bolus injection has the surprisingly advantage of a lower decrease of the plasma fibrinogen in contrast to the single bolus injection of the same total dosage. The size of the second bolus in the double bolus administration can thereby be made variable without limiting the success.

EXAMPLE 3

The thrombolytically active protein K1K2P referred to supra was used for this example. It is non-glycosylated because it is produced by recombinant DNA technology in E. coli cells, has a specific activity of 650,000±200,000 U/mg, and has a dominant half life in dogs of 10.7±1.5 min (mean ±SD; n=6) which is 6.7-fold longer than that of rt-PA (1.6±0.2 min; n=6) at identical doses of 200 ku/kg and as measured by an activity assay as described below. Since the half life of rt-PA varies with the dose, the pharmacokinetics of wild type t-PA at 800 ku/kg (=1 mg/kg) was evaluated. At this dose, the half life was 2.93±0.23 min. Therefore, relative to wt-tPA at 800 ku/kg, K1K2P had a 3.7-fold longer half life than t-PA (range: 3.7–6.7). FIG. 6 illustrates the different plasma concentration time curves of K1K2P and rt-PA after i.v. bolus injection of 200 kU/kg in anesthetized dogs.

The plasma concentration of activity of the thrombolytically active proteins, K1K2P and rt-PA were measured by plasminogenolytic assay as described by Verheijen et al. (Thromb. Haesmostas 1982; 48: 266–269). Briefly, 9 parts of blood were combined with 1 part citrate (final concentration 11 mM) for preparation of plasma samples using standard techniques, which were stored, deep frozen, until assayed. Inhibitors were removed from the thawed plasma by preparation of euglobulin fractions. The plasminogenolytic activity was measured by an indirect spectrophotometric method. CNBr split products of human fibrinogen were used for stimulation of the thrombolytically active proteins to activate Glu plasminogen added to the sample to plasmin which reacted with the synthetic plasmin substrate Tos-Gly-Pro-Lys-4-NA (CHROMOZYM™PL, Boehringer Mannheim, Mannheim Germany) as the chromogenic substrate. A t-PA standard calibrated using the international standard for t-PA, as established by the National Institute for Biological Standards and Control (Holly Hill, Hampstead, London, UK).

The canine model of coronary artery thrombosis as described supra was used for the present study. Briefly, adult beagle dogs of either sex (n=4–5 per group) were anesthetized, catheterized and surgically prepared in order to produce a left circumflex arterial thrombus by electrolytic injury. The thrombus was allowed to age for 60 min prior to administration of fibrinolytic agents (t=0 h). The animals were anticoagulated by i.v. bolus injection of 100 IU/kg heparin at t=−45 min immediately followed by an intravenous infusion of heparin at a dose of 50 IU/kg/h for the remainder of the experiment. K1K2P was administered either as a single i.v. bolus injection of 0.64 mg/kg (=416 kU/kg) over 1 min (t=0–1 min) to 5 dogs or as a double bolus i.v. injection of, at first, 0.32 mg/kg (=208 kU/kg) at t=0–1 min followed by a second bolus injection of 0.32 mg/kg (=208 kU/kg) over 1 min 30 min apart (at t=30–31 min). The double bolus group consisted of 4 dogs. Thrombolysis parameters were as follows: the time to reperfusion, the incidence of reperfusion, and the maximum of coronary blood flow (CBF) after reperfusion. The cumulative patency time describes the sum of time intervals after reperfusion in which coronary blood flow was present. Blood samples were taken on citrate in order to measure plasma fibrinogen with a clotting rate method according to Clauss, Acta haemat. 17: 237–246 (1957).

After single bolus injection of 0.64 mg/kg K1K2P, 60% (3/5) of the dogs reperfused at 23±14 min, whereas in the double bolus group 100% (4/4) of the animals achieved reperfusion at 16±10 min. The reperfused coronary arteries remained open for an average of 129±35 min (=CPT) after double bolus injection, which is twice that of the single bolus group, and is also better than the single bolus group (CPT=63±77 min) (see Table 5 and FIG. 7). The table summarizes the thrombolysis parameters. FIG. 7 demonstrates the time course of coronary blood flow after single bolus injection of 0.64 mg/kg K1K2P and double bolus injection of 0.32+0.32 mg/kg, 30 min apart. In contrast to the single bolus injection of K1K2P, the double bolus regimen of K1K2P was able to achieve a higher level and quality of blood flow and prevented reocclusion after successful reperfusion. In addition, the double bolus regimen of K1K2P induced less fibrinogen reduction that the single bolus regimen (residual fibrinogen=83% vs. 65%, respectively).

TABLE 5

Thrombolysis parameters in the single and double bolus (30 min interval) groups with K1K2P

| Parameter | Single bolus | Double bolus |
|---|---|---|
| K1K2P dose (mg/kg) | 0.64 | 0.32 + 0.32 |
| Incidence of reperfusion (%) | 3/5 (=60%) | 4/4 (=100%) |
| Time to reperfusion (min) | 23 ± 14 | 16 ± 10 |
| Cumulative patency time (min) | 63 ± 77 | 129 ± 35 |
| Coronay blood flow maximum (ml/min) | 8.2 ± 7.6 | 13 ± 5.5 |
| Residual fibrinogen (% of the initial value) | 65 ± 37 | 83 ± 13 |

Mean ± SD

EXAMPLE 4

The present study shows that the combination of very early administration of heparin and thrombolytically active protein in treatment of coronary artery thrombosis in a canine model. Commercially available wt-tPA has a specific activity of 800,000 U/mg. The canine model of left circumflex coronary artery thrombosis was used as described in examples 1, 2 and 3. Briefly, adult beagle dogs of either sex were anesthetized, catheterized, and surgically prepared and instrumented for induction of the coronary artery thrombus. The coronary artery was instrumented with a flow probe to measure coronary blood flow. Zero flow indicated thrombosis; an increase indicated restoration of blood flow (reperfusion) and a decrease to zero indicated reocclusion.

The thrombus was allowed to age for one hour prior to administration of the fibrinolytic agent (t=0 h). One group of animals (n=4) was anticoagulated with intravenous heparin. Anticoagulation was initiated at t=−45 min, i.e., before administration of alteplase, by an i.v. loading bolus injection of 100 IU/kg of heparin, followed by an i.v. continuous infusion of 50 IU/kg/h heparin. The second group (n=4) received saline-placebo instead of very early heparin, i.e., these animals received an i.v. bolus injection of 1 ml/kg saline at t=−45 min followed by an i.v. continuous infusion of 1 ml/kg/h saline. All animals in both groups received a double bolus injection of 0.705+0.705 mg/kg alteplase, 30 min apart, i.e., the first bolus was injected at t=0−1 min and the second bolus at t=30−31 min. Coronary blood flow was followed for three hours after the first bolus injection of alteplase.

Blood samples were taken on citrate as in example 3, to measure activated partial thromboplastin time (aPTT) which is a parameter to control effective anticoagulation with heparin and should be 2–3 times higher than baseline. Additionally, plasma fibrinogen was measured by the clotting rate method according to Clauss supra. Thrombolysis parameters were as follows: the incidence of reperfusion, the time to reperfusion, the maximum or coronary blood flow after reperfusion. The cumulative patency time describes the sum of time intervals after reperfusion in which coronary artery blood flow as present.

Without heparin, only 2/4 (=50%) of the dogs receiving double bolus alteplase demonstrate reperfusion. However, the dogs without heparin had a very poor coronary blood flow and reoccluded soon after reperfusion (FIG. 8). In contrast, the administration of heparin beginning prior to alteplase resulted in a higher incidence of reperfusion (75%), a higher maximum of coronary blood flow after reperfusion and, most importantly, a longer cumulative patency time (CPT) of 74 min with heparin versus only 8 min without heparin (table 6). The desired range of 2–3 fold prolongation of the aPTT (2.6-fold) was achieved when heparin was used. The data demonstrate that very early heparin is desirable in administration of multiple boli of thrombolytically active protein in order to improve thrombolysis and especially, to prevent the tendency to reocclude which is observed after double bolus administration without heparin for some thrombolytically active protein, such as rt-PA.

TABLE 6

Thrombolysis parameters in the double bolus (db) alteplase groups (0.705 + 0.705 mg/kg; 30 min interval) with heparin administration beginning prior to alteplase and with no heparin (but saline)

| Parameter | Saline + db alteplase | Heparin + db alteplase |
|---|---|---|
| Incidence of reperfusion (%) | 2/4 (=50%) | 3/4 (=75%) |
| Time to reperfusion (min) | 32 ± 16 | 62 ± 80 |
| Cumulative patency time (min) | 8 ± 11 | 74 ± 58 |
| Coronary blood flow maximum (ml/min) | 7 ± 10 | 12 ± 8 |
| Residual fibrinogen (% of the initial value) | 78 ± 16 | 81 ± 6 |
| aPTT prolongation (-fold baseline) | 1.1 ± 0.05 | 2.6 ± 0.5 |

Mean ± SD; aPTT, activated partical thromboplastin time.

EXAMPLE 5

A "Phase II" study was carried out in which the thrombolytically active protein BM 06.022 was compared to wild type t-PA.

In these experiments, patients suffering from a coronary arterial occlusion were administered either wild type t-PA, or the protein of the invention. The wild type t-PA was the control, and it was administered in accordance with the approved protocol for the drug. Specifically, 100 mg of wild type t-PA ("wt-tPA") were administered over a period of three hours. The subjects received 60 mg in the first hours, and 20 mg in each of hours 2 and 3. For the K2P compound, 10 MU's of product were administered in 1–2 minutes, followed by a 30 minute break, and then another 10 MU's were administered over 1–2 minutes. The percentage of subjects exhibiting so-called "TIMI-2" and "TIMI-3" were counted. To explain, "TIMI" is used to refer to the occlusive condition of a subject's blood vessel. A TIMI-0 value means that there is no flow. TIMI-1 refers to minimal flow; TIMI-2 refers to delayed perfusion, while TIMI-3 refers to complete reperfusion.

When subjects were examined 30 minutes after the drug was administered, 61.2% of the subjects given BM 06.022 showed TIMI-3 or TIMI-2 values (forty-nine patients overall). Of these, 30.6% showed TIMI-3. Of the 50 patients receiving rt-tPA, 52% showed TIMI-3 or TIMI-2, with 24% showing TIMI-3.

The p-values for BM 06.022 versus wt-tPA were determined, both for patency and TIMI-3. These were 0.35 and 0.46, respectively.

In the same study, a second antiogram was taken at 60 minutes, using 100 patients (wt-tPA), and 95 patients (BM 06.022), and values were secured after 60 minutes. For BM 06.022, the total TIMI-3 and TIMI-2 as 79.0%, of which 52.6% were TIMI-3, compared to 66.0% (33% TIMI-3) for wt-tPA. When p-values were calculated (patency and TIMI-3), for BM 06.022 versus wt-tPA, these were 0.043 and 0.006, respectively.

When results were determined after 90 minutes, BM 06.022 showed 85.4% TIMI-2 and TIMI-3, of which 62.8% was TIMI-3, as compared to 76.6% (47.6%) for wt-tPA. Again, p-values were determined, and these were 0.059 (patency), and 0.01 (TIMI-3).

A follow up angiogram in the study was also performed, where subjects were given an angiogram anywhere from five days to three weeks after the last dose of the drug. There were 116 subjects who had been administered BM 06.022. of these, 94.8% were TIMI-3 or TIMI-2 (87.1% TIMI-3), compared to 87.4% of the 119 subjects given wt-tPA (71.4% TIMI-3). The p-values were again determined. For patency, BM 06.022 versus wt-tPA gave a value of 0.046, and the TIMI-3 value was 0.003.

The conclusion which must be reached from these experiments is that the methodology applied is clearly superior to the standard dosing regime now used for administration of thromboembolic agents, such as t-PA.

EXAMPLE 6

Another set of experiments studied reocclusion rates, mortality, and after effects of the drug administration.

In the reocclusion study, subjects were examined, via angiogram, 90 minutes after administration of the drug and two days after administration to determine if reocclusion had occurred.

For the 116 subjects studied who had received BM 06.022 in the protocol of example 5, 2.6% showed reocclusion. In contrast, the reocclusion rate for those who had received wt-tPA (114 patients), was 7%.

For mortality studies, the criterion was simple: how many subject had died 30 days after treatment? Of the 150 subjects who had received BM 06.022, 2% had died, compared to 3.9% of the 153 administered with wt-tPA.

Similarly, subjects were followed to determine if they had suffered from intercranial hemorrhaging, or non-stroke related hemorrhaging. Of the 150 subjects who received BM 06.022, no hemorrhaging was observed, as compared to 3.92% for those receiving wt-tPA (153 subjects, 2.61% interchronial).

For completeness, the demographics of the study follow. Where the results presented supra refer to less than 153 or 150 subjects, it simply means that all patients were unavailable for that phase of the study.

It will be understood that the specification and examples are illustrative but not limitative of the present invention and that other embodiments within the spirit and scope of the invention will suggest themselves to those skilled in the art.

We claim:

1. Method for preventing occlusion or reocclusion comprising administering to a subject with a thromboembolic condition an amount of a thrombolytically active protein which has a half-life greater than recombinant t-PA sufficient to prevent occlusion, in the form of two or more boli, and heparin, wherein said heparin is administered together with said thrombolytically active protein.

2. The method of claim 1, wherein said thrombolytically active protein has a half-life which is greater than that of recombinant human t-PA.

3. The method of claim 2, wherein said thrombolytically active protein has a half-life that is from 2 to 30 times that of recombinant human t-PA.

4. The method of claim 2, wherein said thrombolytically active protein has a half-life of from 10 to 40 minutes.

5. The method of claim 2, wherein said thrombolytically active protein is administered in a dose of from 3–50 MU per bolus.

6. The method of claim 2, comprising administering said two or more boli at an interval of from 10 minutes to 90 minutes therebetween.

7. The method of claim 1, comprising administering a first bolus of said thrombolytically active protein at a dose of from 5–20 MU, and a second bolus of said thrombolytically active protein at a dose of 3–15 MU.

8. The method claim 1, wherein said thrombolytically active protein consists of the K2 and P regions of human t-PA.

9. The method of claim 1, wherein said thrombolytically active protein consists of amino acids of SEQ ID NO: 1.

10. The method of claim 1, wherein said thrombolytically active protein consists of amino acids 1–5 and 88–527 of human t-PA.

11. The method of claim 1, wherein said thrombolytically active protein is unglycosylated.

12. The method of claim 1, wherein said thromboembolic condition is myocardial infarct, a lung embolism, a brain stroke, or an occlusive disease of the circulatory system.

* * * * *

UNITED STATES PATENT AND TRADEMARK OFFICE
CERTIFICATE OF CORRECTION

PATENT NO. : 6,235,279 B1
DATED : May 22, 2001
INVENTOR(S) : Martin et al.

It is certified that error appears in the above-identified patent and that said Letters Patent is hereby corrected as shown below:

<u>Title page,</u>
Foreign Application Priority Data, change "Apr. 15, 1992" to -- Apr. 16, 1991 --.

<u>Column 3,</u>
Line 49, after "increased" delete -- o --.

<u>Column 5,</u>
Line 29, change "257" to -- 527 --.

<u>Column 6,</u>
Line 26, after "be" delete -- o. --.

<u>Column 7,</u>
Line 32, after "BM" delete -- O --.

<u>Column 11,</u>
Line 43, change "U/mg" to -- IU/mg --.

Signed and Sealed this

Twenty-eighth Day of May, 2002

Attest:

Attesting Officer

JAMES E. ROGAN
*Director of the United States Patent and Trademark Office*

UNITED STATES PATENT AND TRADEMARK OFFICE
CERTIFICATE OF CORRECTION

PATENT NO. : 6,235,279 B1
DATED : May 22, 2001
INVENTOR(S) : Martin et al.

It is certified that error appears in the above-identified patent and that said Letters Patent is hereby corrected as shown below:

<u>Title page,</u>
Foreign Application Priority Data, change "Apr. 15, 1992" to -- Apr. 16, 1991 --.

<u>Column 3,</u>
Line 49, after "increased" delete -- o --.

<u>Column 5,</u>
Line 29, change "257" to -- 527 --.

<u>Column 6,</u>
Line 26, after "be" delete -- o. --.

<u>Column 7,</u>
Line 32, after "BM" delete -- O --.

<u>Column 11,</u>
Line 43, change "U/mg" to -- IU/mg --.

This certificate supersedes Certificate of Correction issued May 28, 2002 since theis patent number did not appear on Certificate of Correction listing for May 28, 2002.

Signed and Sealed this

Sixteenth Day of July, 2002

*Attest:*

*Attesting Officer*

JAMES E. ROGAN
*Director of the United States Patent and Trademark Office*